United States Patent [19]

Ecke, Jr.

[11] Plant 5,150

[45] Nov. 29, 1983

[54] POINSETTIA PLANT NAMED R-13

[76] Inventor: Paul Ecke, Jr., Encinitas, Calif. 92024

[21] Appl. No.: 339,783

[22] Filed: Jan. 15, 1982

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Chas. W. Rummler

[57] ABSTRACT

A new, red poinsettia plant having the overall beauty of the Eckespoint C-1 Red (U.S. Plant Pat. No. 2923) and being especially distinguished by blooming at least two weeks earlier, a characteristic made possible by growing at the lower temperature, 15° to 17° C., of the Annette Hegg line of poinsettias. This variety has abundant foliage of a noticeably darker color than that usually found in common commercial varieties and its bright red, tightly centered and imbricated bracts provide a full and compact display of color above the sharply contrasting foliage when the plant is in full bloom.

2 Drawing Figures

BACKGROUND OF THE NEW PLANT

This new poinsettia cultivar originated as a seedling of unknown parentage produced by my crossing unknown seedlings and other commonly known poinsettia varieties in an intensive program of hybridization carried on by me at Encinitas, Calif. This plant was discovered by me in my greenhouses during evaluation of breeding traits and noticed because of its early blooming characteristics and its beautiful bright red bract color, which had qualities similar to the Eckespoint C-1 Red (U.S. Plant Pat. No. 2,923). Propagation under my direction, by cuttings from the parent plant, has been done through successive generations at Encinitas, Calif., and its novel and distinctive characteristics have been found to hold true from generation to generation and appear to be firmly fixed.

DESCRIPTION OF THE DRAWINGS

This new variety of poinsettia is illustrated by the accompanying full color photographic drawings, sheet 1 showing its red color in a face view of the flowers and bracts of a mature bloom and sheet 2 showing a potted plant of this variety in full bloom to illustrate its form and growth habit.

DESCRIPTION OF THE NEW PLANT

The following is a detailed description of my new variety plant as observed in greenhouse at Encinitas, Calif., during the late Fall of 1979, the color designations being according to The R.H.S. Colour Chart published by The Royal Horticultural Society of London, England.

THE PLANT

Origin: Seedling.

Parentage: Unknown.

Classification:

*Botanic.*—*Euphorbia pulcherrima.*

*Commercial.*—Greenhouse Poinsettia.

Form: Shrub.

Height: Medium.

Growth habit:

*As a single stem.*—Upright and vigorous; may require a growth regulator.

*As a branched plant.*—Upright; with a soft pinch, three or four shoots can be expected.

Growth rate: Very fast.

*Rooting.*—Occurs in 15 to 20 days under automatic mist and the plant will bloom in about 8 to 9 weeks at a night temperature of 15° to 17° C. during October and November. Under poor light conditions, a somewhat higher temperature may be required.

Foliage: Alternate horizontal to upward rising, with medium persistence and in normal abundance.

*Leaf size.*—About 13 to 18 cm. long and about 10 to 15 cm. wide.

*Leaf shape.*—Ovate with acuminate apex and usually sharply bi-lobed on each side of the mid-rib. Some leaves have 1 to 3 lobes which occasionally are only rudimentary.

*Aspect.*—Upper side — Dull with vein indented. Under side — Dull with ordinary veining.

*Color.*—Upper side — Very dark green; between RHS 139A and 147A but somewhat darker. Under side — Between RHS 137A and 147A.

*Retention.*—The foliage lasts well when kept at low room temperature, that is below 20° C., and with good light intensity.

Bracts: Generally about 15 to 20 in number, in a generally imbricated arrangement with a tight center providing a full appearance; Often some bracts twist rather than lie in a flat plane and, in general, the bracts have a somewhat cascading effect.

*Size.*—Various. Up to about 20 cm. long and about 15 cm. wide.

*Shape.*—Substantially the same as the leaves. Small or immature bracts are usually elliptic and acuminate.

*Petioles.*—Quite short, about 50 mm. to 4 cm. long.

*Color.*—Upper side — Bright red near and between RHS 45A, 45B and 46B. Under side — Near RHS 53C.

*Ribs and veins.*—The ribs and larger veins protrude from beneath the under surface of the bracts and are of a purplish tone as compared to the red of the bracts.

*Retention.*—The bracts have medium persistence, similar to that of the Eckespoint C-1 Red variety.

*Flower.*—The nectar cups are colored near RHS Yellow-Orange 23A.

This new variety of red poinsettia plant has the beauty of the well known Eckespoint C-1 Red (U.S. Plant Pat. No. 2,923) but it has the distinct advantage of an earlier blooming habit at a lower temperature. This plant is medium tall in height and responds well to growth regulators. The cyanthia cluster is compact and because the bract petioles are usually very short, the plant provides a full and compact display of color when in full bloom. The color is an intense red, which has a good resistance to fading with age, and the very dark green leaves generally do not show chlorotic symptoms. It is very important, however, to provide proper nutrition, including trace elements, for the best plant growth and health.

I claim:

1. A new and distinctive red poinsettia cultivar, substantially as herein shown and described, characterized by its bright dark red bract color and its early, eight to ten week, blooming characteristic at a low growing temperature, generally in the range of 15° to 17° C.

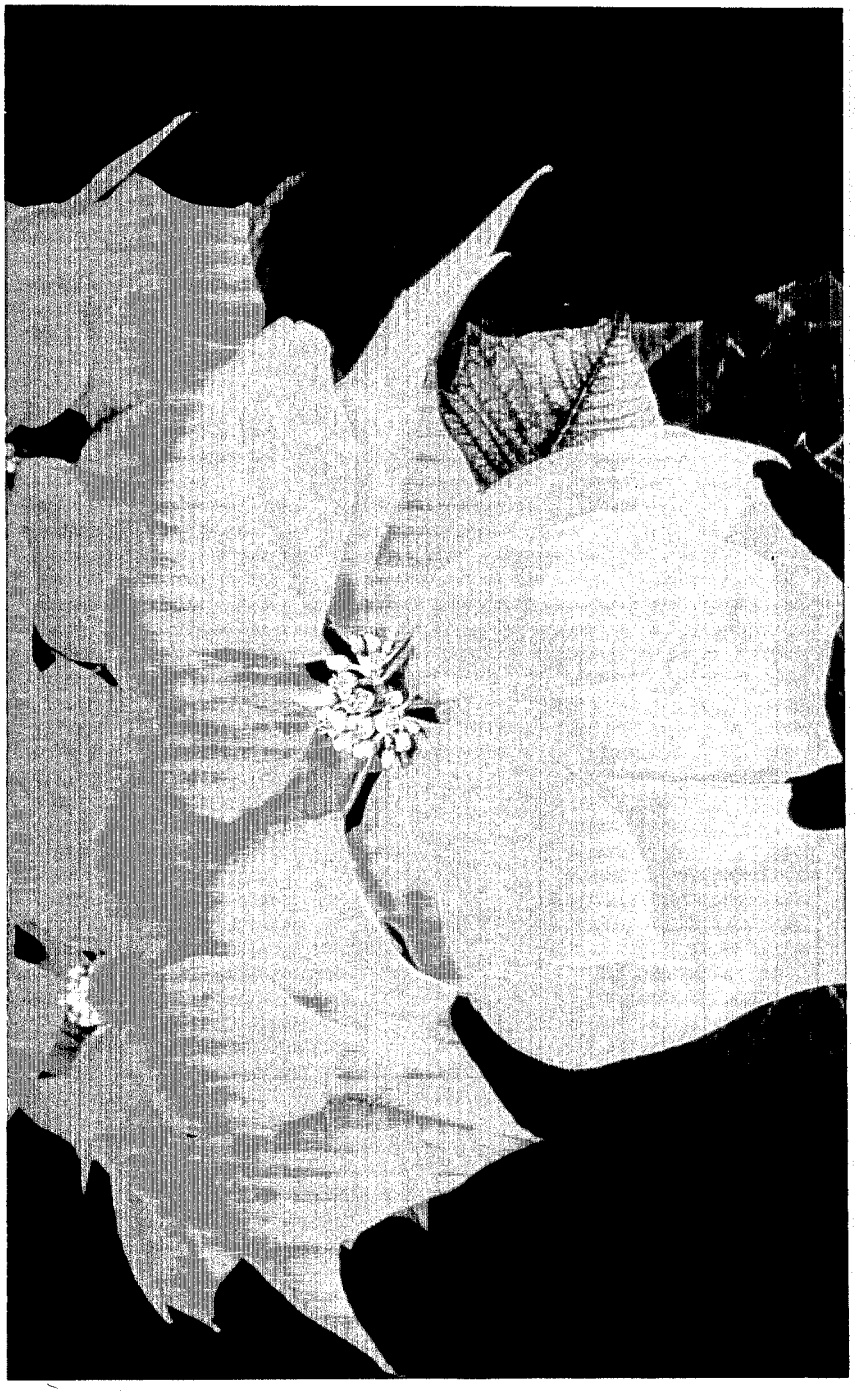

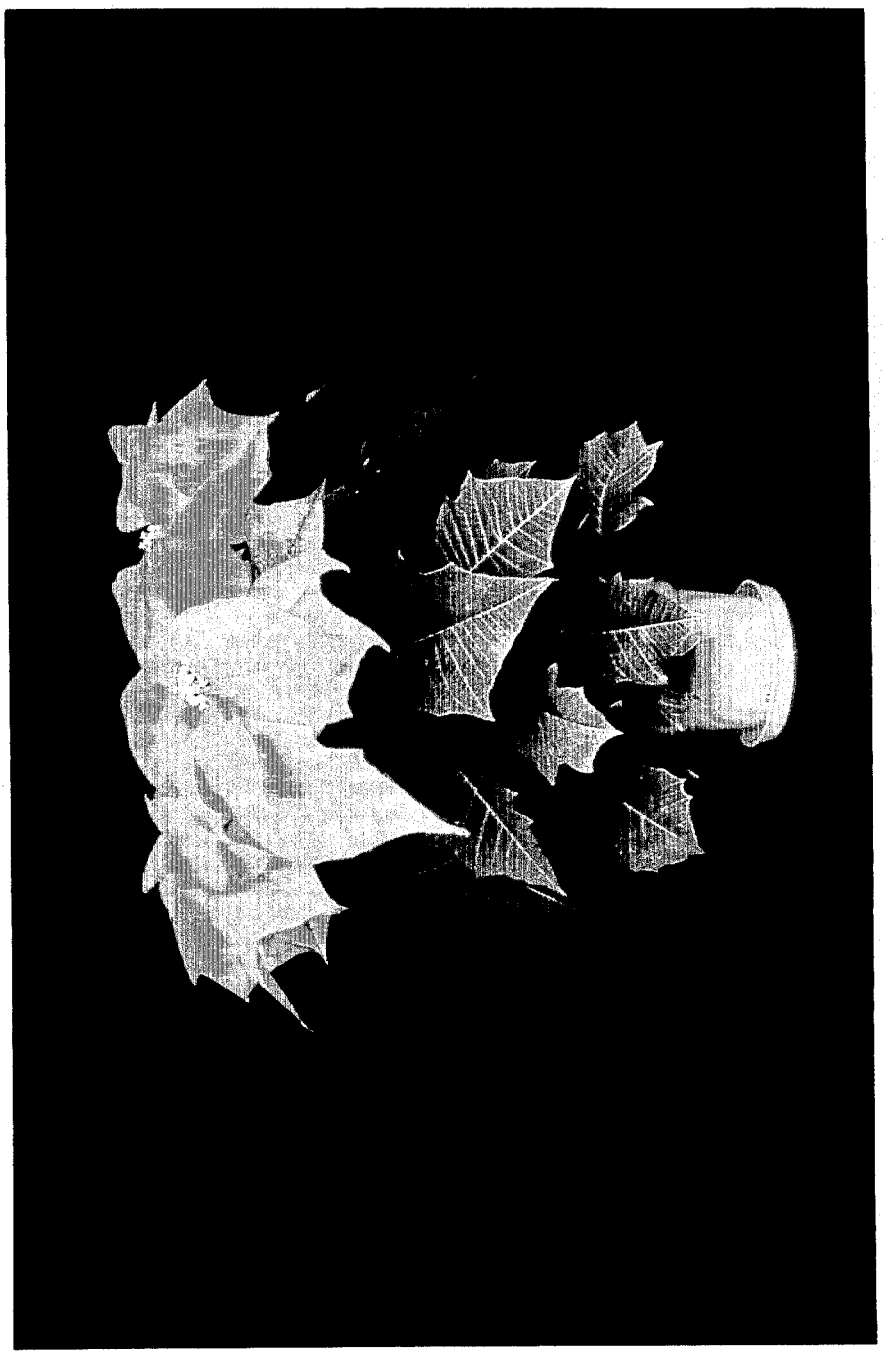

* * * * *